US00PP27894P3

(12) United States Plant Patent
Meilland

(10) Patent No.: US PP27,894 P3
(45) Date of Patent: Apr. 18, 2017

(54) FLORIBUNDA ROSE PLANT NAMED 'MEIANYCID'

(50) Latin Name: *Rosa hybrida*
Varietal Denomination: Meianycid

(71) Applicant: CP DELAWARE, INC., Wilmington, DE (US)

(72) Inventor: Alain A. Meilland, Antibes (FR)

( * ) Notice: Subject to any disclaimer, the term of this patent is extended or adjusted under 35 U.S.C. 154(b) by 0 days.

(21) Appl. No.: 14/756,107

(22) Filed: Aug. 3, 2015

(65) Prior Publication Data

US 2017/0006745 P1 Jan. 5, 2017

(30) Foreign Application Priority Data

Jun. 30, 2015 (QZ) ..... 2015/1510

(51) Int. Cl.
*A01H 5/02* (2006.01)

(52) U.S. Cl.
USPC ..... Plt./145

(58) Field of Classification Search
USPC ..... Plt./141, 145
See application file for complete search history.

*Primary Examiner* — Susan McCormick Ewoldt
(74) *Attorney, Agent, or Firm* — Buchanan Ingersoll & Rooney PC

(57) ABSTRACT

A new and distinct Floribunda rose plant is provided that commonly commences blooming early in the season and forms abundantly and substantially continuously attractive luminous yellow semi-double blossoms. The growth habit is bushy. Very strong vegetation is formed. The vegetation is very dense and bears a semi-glossy aspect on the upper surface. During observations to date the disease tolerance has been good particularly with respect to black spot. The plant is well suited for providing attractive ornamentation in parks and gardens.

1 Drawing Sheet

Figures 1, 2, 3, 4, 5, 6, 7, 8, 9, 10, 11, 12, 13, 14, 15, 16:
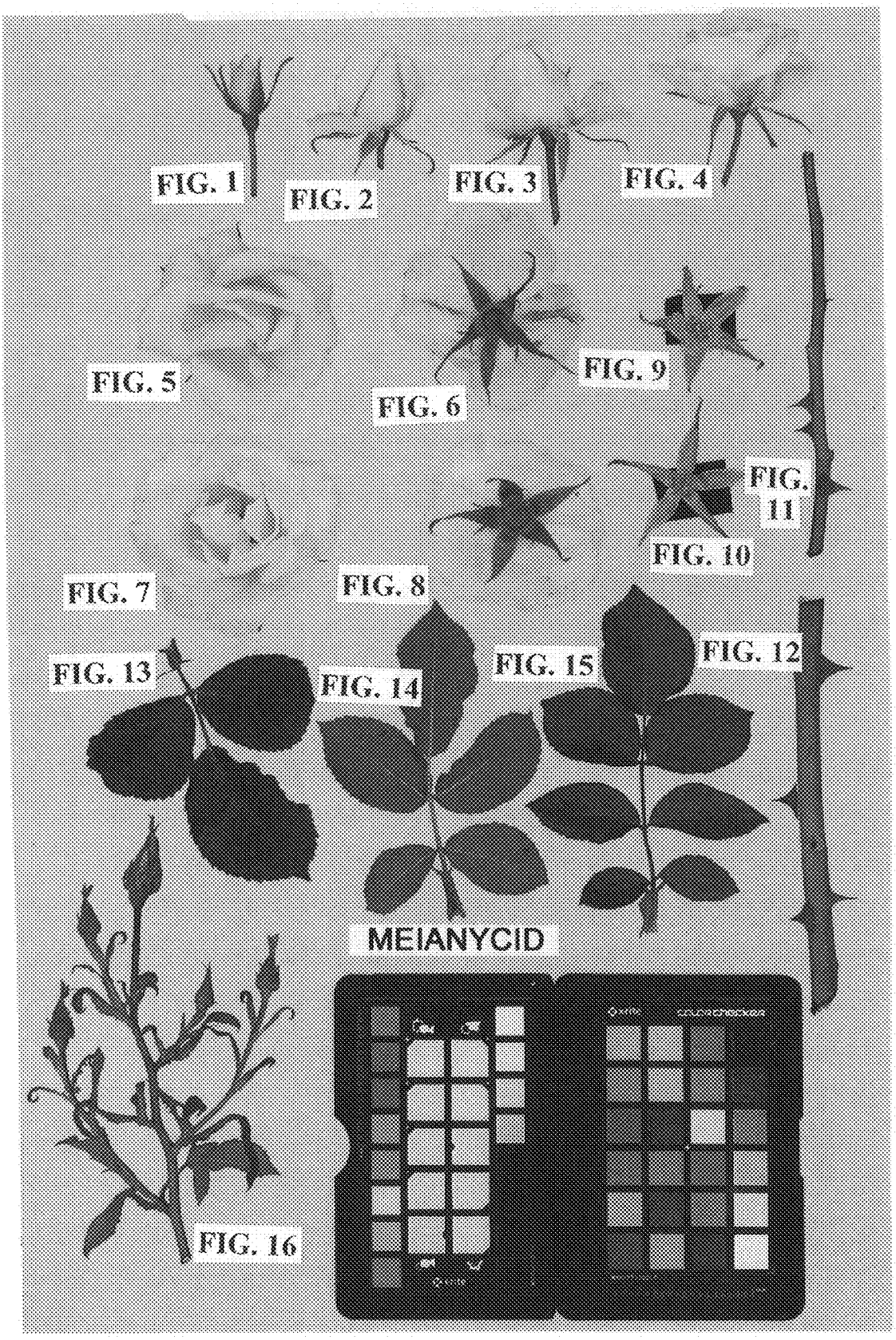

Botanical/commercial classification: *Rosa hybrida*/Floribunda Rose Plant.

Varietal denomination: cv. Meianycid.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the product of the cross of the 'Delbaf' variety (non-patented in the United States) and an unnamed and unreleased seedling (non-patented in the United States). The male parent (i.e., the pollen parent) was the 'Harkuly' variety (non-patented in the United States). The 'Harkuly' variety sometimes is known as the 'Margaret Merril' variety.

The parentage of the new variety can be summarized as follows:

('Delbaf'×Unnamed Seedling)×'Harkuly'.

The seeds resulting from the above pollination were sown and small plants were obtained which were physically and biologically different from each other. Selective study resulted in the identification of a single plant of the new variety.

It was found that the new Floribunda rose plant of the present invention:

(a) displays a bushy growth habit with very strong vegetation,
(b) forms in abundance on a substantially continuous basis attractive luminous yellow semi-double blossoms, (c) exhibits very dense dark green foliage with a semi-glossy aspect on the upper surface that contrasts nicely with the blossom coloration,
(d) displays good tolerance to disease particularly with respect to black spot, and
(e) is well suited for providing attractive ornamentation in parks and gardens.

The blooming tends to commence early in the season during observations to date.

The new variety well meets the needs of the horticultural industry and can be grown to advantage in the landscape where attractive ornamentation is to be provided.

The new variety can be readily distinguished from its ancestors and other known cultivars. For instance, the new variety displays yellow blossoms while the 'Delbaf' variety displays blossoms having an ochre coloration, the 'Harkuly' variety (male parent) forms white blossoms, and the female parent forms bicolor lavender-yellow blossoms.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meianycid'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during July while growing outdoors their own roots at Le Cannet des Maures, Var, France. Standard color information is included at the lower-right portion of the photograph.

FIG. 1—illustrates a specimen of a floral bud at the opening of the sepals;

FIG. 2—illustrates a specimen of a floral bud wherein the sepals are more fully open;

FIG. 3—illustrates a specimen of a floral bud at the opening of the petals;

FIG. 4—illustrates a specimen of a flower in the course of opening;

FIG. 5—illustrates a specimen of an open flower—plan view—obverse;

FIG. 6—illustrates a specimen of an open flower—plan view—reverse;

FIG. 7—illustrates a specimen of a fully open flower—plan view—obverse;

FIG. 8—illustrates a specimen of an open flower—plan view—reverse;

FIG. 9—illustrates a specimen of a floral receptacle showing the arrangement of the stamens and pistils;

FIG. 10—illustrates a specimen of a floral receptacle showing the arrangement of the pistils (stamens removed);

FIG. 11—illustrates a specimen of a flowering stem;

FIG. 12—illustrates a specimen of a main branch;

FIG. 13—illustrates a specimen of a leaf with three leaflets—plan view—upper surface;

FIG. 14—illustrates a specimen of a leaf with five leaflets—plan view—under surface;

FIG. 15—illustrates a specimen of a leaf with seven leaflets—plan view—upper surface; and FIG. 16—illustrates a cluster of floral buds.

DETAILED BOTANICAL DESCRIPTION

The chart used in the identification of the colors is that of The Royal Horticultural Society (R.H.S. Colour Chart, 1995 Edition). The description is based on the observation of two-year-old plants during July while growing outdoors on their own roots at Le Cannet des Maures, Var, France.

Class: Floribunda.

Plant:

*Growth habit*.—Bushy.

*Height*.—Approximately 100 cm on average.

*Spread*.—Approximately 70 cm on average.

Branches:

*Color*.—Young stems: near Yellow-Green Group 146B. Adult wood: near Yellow-Green Group 146B.

*Thorns*.—On young stems: Configuration: with an oval base. Quantity: approximately 5 on average on a stem length of 10 cm. Length: approximately 1.1 cm on average. Color: near Greyed-Purple Group 181D. On adult stems: Configuration: elongated and curved downwards on the upper surface and concave on the under surface with an oval base. Quantity: approximately 10 on average on a stem length of 10 cm. Length: approximately 1.1 cm on average. Color: near Greyed-Orange Group 166A and 166B.

Leaves:

*Size*.—Overall size of a 5-leaflet leaf: length: approximately 10-11 cm on average; width: approximately 8.5-9.0 cm on average.

*Stipules*.—Adnate, pectinate, rather broad, approximately 2.7 cm in length on average, approximately 7 mm in width on average, near Green Group 137B on the upper surface, and near Green Group 138B on the under surface.

*Petioles*.—Upper surface: near Green Group 137B in coloration. Under surface: near Green Group 138B in coloration. Length: commonly approximately 3 cm on average for a terminal leaflet. Texture: non-glandular on the upper surface, and with a few small prickles on the under surface.

*Rachis*.—Upper surface: near Yellow-Green Group 145A in coloration. Under surface: near Green Group 138B in coloration.

*Leaflets*.—Number 3, 5 and 7 (most often). General appearance: dense dark green. Shape: generally elliptical with a generally cuspidate tip and an obtuse base. Size: the terminal leaflets commonly are approximately 5.2 cm in length on average and approximately 3.9 cm in width on average. Serration: slightly denticulate, small and single (as illustrated). Texture: physically firm and leathery with a semi-glossy upper surface. Color (young foliage): Upper surface: near Yellow-Green Group 146A. Under surface: near Yellow-Green Group 146C. Color (adult foliage): Upper surface: near Green Group 137A. Under surface: near Green Group 137C. Venation: Pattern: alternate pinnate. Color: near Yellow-Green Group 146B.

Inflorescence:

*Number of flowers*.—Commonly approximately 5 to 10 blossoms per stem.

*Peduncle*.—Smooth, approximately 4.5 cm in length on average, approximately 2 mm in diameter on average, and near Green Group 138A in coloration.

*Sepals*.—Upper surface: tomentose and near Yellow-Green Group 148B and 148C in coloration. Under surface: smooth and near Green Group 138A in coloration. Shape: longish and narrow, and somewhat upright at the base. Size: approximately 2.9 to 3.2 cm in length on average, and approximately 6 mm in width at the widest point on average.

*Buds*.—Shape: substantially conical. Size: small. Length: approximately 1.8 cm on average. Width: approximately 1.5 cm at the widest point on average. Color as calyx breaks: Upper surface: near Yellow Group 12A. Under surface: near Yellow Group 12A.

*Flower*.—Shape: cup-shaped. Diameter approximately 8 cm on average. Depth: approximately 3.5-4.0 cm on average. Color (in the course of opening): Upper surface: near Yellow-Group 12A. Under surface: near Yellow Group 12A. Color (open flower): Upper side: near Yellow Group 12A suffused with near Yellow Group 7A. Under side: near Yellow Group 7A. Fragrance: none detected. Petal number: approximately 16 on average under normal growing conditions. Petal shape: with a substantially rounded tip and a rounded base. Petal texture: leathery and somewhat firm. Petal length: approximately 4 cm on average. Petal width: approximately 3.9 cm on average. Petal arrangement: imbricated, and without petaloids. Petal drop: good with the petals commonly detaching cleanly before drying. Stamen number: approximately 97 on average. Anthers: regularly arranged around the styles, approximately 1 mm in size on average, and near Yellow-Orange Group 14B in coloration. Filaments: approximately 3 to 5 mm in length on average, and near Yellow Group 14B in coloration. Pollen: none available for observation. Pistils: approximately 65 on average. Stigmas: approximately 1 mm in size on average, and near Yellow Group 2D in coloration. Styles: approximately 3 mm in length on average, and near Red Group 45B in coloration. Receptacle: smooth, funnel-shaped in longitudinal section, approximately 5 mm in length on average, approximately 6 mm in width on average at the widest point, and near Green Group 138A in coloration.

Development:

*Vegetation*.—Very strong.

*Blooming*.—Early season, very abundant and substantially continuous.

*Tolerance to disease*.—Very good, particularly with respect to black spot.

The new 'Meianycid' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) displays a bushy growth habit with very strong vegetation, (b) forms in abundance on a substantially continuous basis attractive luminous yellow semi-double blossoms, (c) exhibits very dense dark green foliage with a semi-glossy aspect on the upper surface, (d) displays good tolerance to disease particularly with respect to black spot, and (e) is well suited for providing attractive ornamentation in parks and gardens;

substantially as shown and described.

* * * * *

MEIANYCID